US007482585B2

(12) United States Patent
Sando et al.

(10) Patent No.: US 7,482,585 B2

(45) Date of Patent: Jan. 27, 2009

(54) TESTING CHIP AND MICRO INTEGRATED ANALYSIS SYSTEM

(75) Inventors: Yasuhiro Sando, Amagasaki (JP); Akihisa Nakajima, Sagamihara (JP); Kusunoki Higashino, Osaka (JP)

(73) Assignee: Konica Minolta Medical & Graphic, Inc., Tokyo (JP)

(*) Notice: Subject to any disclaimer, the term of this patent is extended or adjusted under 35 U.S.C. 154(b) by 434 days.

(21) Appl. No.: 11/434,253

(22) Filed: May 16, 2006

(65) Prior Publication Data

US 2006/0263914 A1 Nov. 23, 2006

(30) Foreign Application Priority Data

May 19, 2005 (JP) ............................ 2005-147035

(51) Int. Cl.
*F15C 1/06* (2006.01)
*B01D 27/26* (2006.01)

(52) U.S. Cl. ....................... 250/288; 250/281; 250/285; 137/883; 422/100

(58) Field of Classification Search ....................... None
See application file for complete search history.

(56) References Cited

U.S. PATENT DOCUMENTS 5,969,353 A * 10/1999 Hsieh ......................... 250/288
6,176,962 B1 * 1/2001 Soane et al. ................ 156/292
6,296,020 B1 * 10/2001 McNeely et al. ............ 137/806
6,459,080 B1 * 10/2002 Yin et al. .................... 250/288
6,803,568 B2 * 10/2004 Bousse et al. .............. 250/288
6,812,457 B2 * 11/2004 Andersson et al. .......... 250/288
7,105,812 B2 * 9/2006 Zhao et al. .................. 250/288
7,128,876 B2 * 10/2006 Yin et al. .................... 422/100
7,282,705 B2 * 10/2007 Brennen ..................... 250/288
7,387,765 B2 * 6/2008 Chen et al. .................. 422/100
7,391,020 B2 * 6/2008 Bousse et al. .............. 250/288
7,412,990 B2 * 8/2008 Chung et al. ................ 137/833

* cited by examiner

*Primary Examiner*—David A. Vanore
(74) *Attorney, Agent, or Firm*—Finnegan, Henderson, Farabow, Garrett & Dunner, L.L.P.

(57) ABSTRACT

A testing chip includes (1) a first chip having a micro flow path that stores reagent; upstream-side opening provided on upstream-side of the micro flow path; downstream-side opening provided on downstream-side of the micro flow path; and one or more sealing members in a small thickness stuck to at least one surface of the first chip to seal the upstream-side opening and the downstream-side opening until the testing chip is used and (2) a second chip having a micro flow path for mixing and reaction between reagent and a specimen and detecting the reaction; and an opening provided on upstream-side of the micro flow path, wherein, when the testing chip is used, the first and second chips are superimposed on each other so that the downstream-side opening of the first chip and the opening of the second chip are positioned on each other.

10 Claims, 15 Drawing Sheets

2 4 6 7 3 11 25 12

1
2
3
4
4
5
5
6 (11)
6 (11)
13
14a
14b
15
15
16a
16b
17
18
19
20

3
11
11
13
15
16a
16b
17
18
19
20
21
21
22
22

34
31
33
38
39
36b
37
32
35
36a

TESTING CHIP AND MICRO INTEGRATED ANALYSIS SYSTEM

This application is based on Japanese Patent Application No. 2005-147035 filed on May 19, 2005, in Japanese Patent Office, the entire content of which is hereby incorporated by reference.

FIELD OF THE INVENTION

The present invention relates to a testing chip including a micro flow path for mixing and reaction between a specimen and reagent and detection of the reaction, and relates to a micro integrated analysis system that uses the testing chip to analyze a target material in the specimen.

BACKGROUND OF THE INVENTION

In recent years, by micro-machine technology and microscopic processing technology, systems have been developed in which devices and means (for example pumps, valves, flow paths, sensors and the like) for performing conventional sample preparation, chemical analysis, chemical synthesis and the like are micronized and integrated on a single chip (Patent Document 1). This is also called μ-TAS (Micro Total Analysis System), bioreactor, lab-on-chips, and biochips, and much is expected of their application in the fields of medical testing and diagnosis, environmental measurement and agricultural manufacturing. As seen in gene testing in particular, in the case where complicated steps, skilful operations, and machinery operations are necessary, a microanalysis system which is automatic, speedy and simple is very beneficial not only in terms of cost, required amount of sample and required time, but also in terms of achieving analyses, regardless of time and place.

In various analyses and tests, the quantitation of analysis, accuracy of analysis and economic factors with such analyzing chips are of great importance. Consequently, it is required to establish a liquid feeding system with a simple structure and highly reliability. A micro fluid control element with high accuracy and excellent reliability is desired. The inventors of the present invention have already offered a micro pump system and a control method thereof that satisfy such requirements (Patent Documents 2 to 4).

[Patent Document 1] TOKKAI No. 2004-28589

[Patent Document 2] TOKKAI No. 2001-322099

[Patent Document 3] TOKKAI No. 2004-108285

[Patent Document 4] TOKKAI No. 2004-270537

In analysis by the use of a micro analysis system, as described above, it is desirable that a predetermined amount of reagent is sealed in advance in a micro flow path formed in a testing chip for analysis so as to perform quick analysis and test upon necessity.

In order to seal reagent in a testing chip in advance, a testing chip is required to prevent evaporation of the reagent during storage prior to use, to prevent leaking of the reagent from a flow path section storing the reagent to an external flow path communicating with the flow path section during storage prior to use, and to be able to easily flow out the reagent from the flow path section storing the reagent to a successive flow path at the time of use.

An object of the invention is to provide a testing chip for analysis of a target material in a specimen and a micro integrated analysis system using the testing chip which prevent reagent, which is sealed in advance at a predetermined position in a flow path, from leaking out to an external path during storage, and let the reagent easily flow out from the flow path in which the reagent is sealed to a successive flow path at the time of use.

SUMMARY OF THE INVENTION

In an aspect of the invention, there is provided a testing chip, including:

(1) a first chip that has:

a micro flow path that stores reagent;

an upstream-side opening provided on an upstream side of the micro flow path;

a downstream-side opening provided on a downstream-side of the micro flow path; and one or more sealing members in a small thickness that are stuck to at least, one surface of the first chip to respectively seal the upstream-side opening and the downstream-side opening until the testing chip is used; and (2) a second chip that has:

a micro flow path for mixing and reaction between reagent and a specimen and detecting the reaction; and an opening provided on an upstream side of the micro flow path, wherein when the testing chip is used, the first and second chips are superimposed on each other such that the downstream-side opening of the first chip and the opening of the second chip are positioned on each other.

DETAILED DESCRIPTION OF THE PREFERRED EMBODIMENTS

Figure 1:
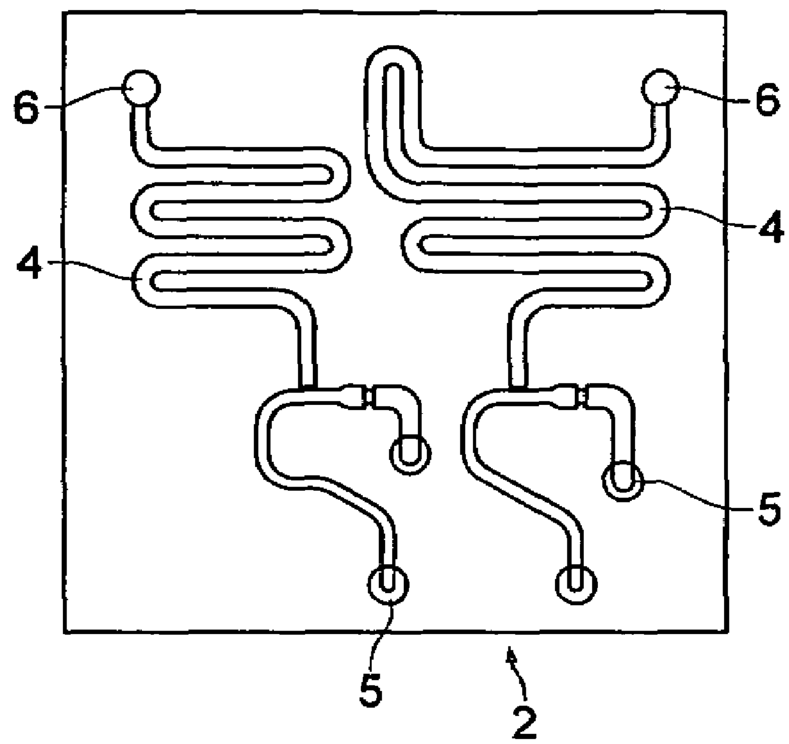
FIG. 1 is a plan view showing a first testing chip in an embodiment in accordance with the invention.

The invention includes the following items.

(Item 1)

A testing chip including:

a first chip provided with a micro flow path that stores reagent;

and a second chip provided with a series of flow paths for mixing and reaction between reagent and a specimen and detection of the reaction, wherein, one or more sealing members in a small thickness are stuck, at least, to one surface of the first chip;

an upstream-side opening provided on the upstream side of the micro flow path of the first chip and a downstream-side opening provided on the downstream side of the micro flow path of the first chip are respectively sealed with the sealing member; and an opening is provided for the micro flow path of the second chip, the opening being to be positioned on the downstream-side opening of the first chip by superimposing the first and second chips on each other at the time of use.

(Item 2)

The testing chip of Item 1, wherein:

the sealing member that seals the downstream-side opening of the first chip is peelable;

the sealing member is peeled off when at the time of use; and thereafter the first and second chips are superimposed on each other so that the micro flow path of the first chip and the micro flow path of the second chip communicate with each other.

(Item 3)

The testing chip of Item 1, wherein:

a needle section in a thin-tube shape is provided at the opening of the second chip;

the first and second chips are superimposed on each other at the time of use so that the needle section penetrates through the sealing member at a position of the downstream-side opening of the first chip, and thereby the micro flow path of the first chip and the micro flow path of the second chip communicate with each other.

(Item 4)

The testing chip of any one of Items 1 to 3, wherein the upstream-side opening of the first chip is positioned on an opening of a micro pump unit in a chip form, the opening of the micro pump unit communicating with a micro pump and the downstream-side of the micro pump.

(Item 5)

The testing chip of Item 4, wherein:

the sealing member that seals the upstream-side opening of the first chip is peelable and peeled off at the time of use;

thereafter, the testing chip of which the first and second chips are superimposed on each other is superimposed on the micro pump unit such that the upstream-side opening of the first chip and the opening of the micro pump unit are positioned on each other so that the micro flow path of the first chip and the micro pump communicate with each other.

(Item 6)

The testing chip of Item 4, wherein the testing chip of which the first and second chips are superimposed on each other at the time of use is superimposed on the micro pump unit that is provided with a needle section in a thin-tube shape at the opening thereof so that the needle section penetrates through the sealing member at the position of the upstream-side opening of the first chip and thereby the micro flow path of the first chip and the micro pump communicate with each other.

(Item 7)

The testing chip of any one of Items 1 to 3, wherein the micro flow path of the second chip is provided with:

an opening A to be positioned on the upstream-side opening of the first chip by superimposing the first and second chips on each other at the time of use;

and a pump-side opening B to be positioned on an opening of a micro pump unit in a chip form, the opening of the micro pump unit communicating with a micro pump and the downstream side of the micro pump.

(Item 8)

The testing chip of Item 7, wherein:

the sealing member that seals the upstream-side opening of the first chip is peelable and peeled off at the time of use; and then, the first and second chips are superimposed on each other so that the micro flow path of the first chip and the micro flow path of the second chip communicate with each other, the micro flow path of the second chip communicating with the pump-side opening.

(Item 9)

The testing chip of Item 7, wherein:

a needle section in a thin-tube shape is provided at the opening A of the second chip;

the first and second chips are superimposed on each other at the time of use so that the needle section penetrates through the sealing member at the position of the upstream-side opening of the first chip, and thereby the micro flow path of the first chip and the micro flow path of the second chip communicate with each other, the micro flow path of the second chip communicating with the pump-side opening B.

As described above, since a testing chip is constructed by a separate first and second chip, and reagent is stored in a flow path of the first chip with the opening of the flow path sealed with a sealing member, the reagent is prevented from leaking out during storage of the testing chip.

At the time of use, the first and second chips are superimposed on each other, and the micro flow paths provided for these chips communicate with each other in such a manner as described above. Thus, it is possible to easily flow out reagent to a successive flow path.

Using a micro pump unit in a chip form provided with an opening that communicates with a micro pump and the downstream side thereof, and superimposing the upstream-side opening of the first chip or the pump-side opening of the second chip, and the opening of the micro pump unit on each other, it is possible to easily make a micro flow path of the testing chip and the micro pump communicate with each other.

(Item 10)

A micro integrated analysis system, including:

the testing chip of any one of Items 1 to 9 and a system main body, wherein the system main body has in a housing thereof:

a micro pump unit in a chip form having a plurality of micro pumps and openings that communicate with the micro pumps and are to be positioned on upstream-side openings of the testing chip;

a driving liquid tank that stores driving liquid that pushes reagent from an upstream-side to a downstream-side of each micro flow path of the testing chip and communicates with the upstream-side of the respective micro pump;

a detection processing device to detect reaction in the testing chip; and a control device that controls the micro pump unit and the detection processing device; and wherein the system analyses a target material in a specimen in a state where the testing chip is mounted on the system main body.

Preferred embodiments in accordance with the invention will be described below, referring to the drawings.

<Testing Chip>

A testing chip in accordance with the invention includes a first and second chip. FIG. 1 is a plan view showing a first chip and FIG. 2 is a plan view showing a second chip of a testing chip in an embodiment of the invention.

As shown in FIG. 1, a flow path 4 in which reagent is sealed is provided inside the first chip 2. (Herein, the flow paths 4 are shown for convenience, however, it is provided inside the chip. Also, in FIGS. 2 and 3, flow paths are shown likewise.) Both end portions of the flow paths 4 are provided with respective openings 5 and 6 that are opening outside from one side of the chip. Each opening 5 on the upstream side is for communication with a micro pump, and each opening 6 on the downstream side is for communication with a micro flow path provided in the second chip 3. The openings 5 and 6 are sealed, as shown in FIG. 4, with sealing members 7 adhered to the chip surface of the first chip.

Figure 2:
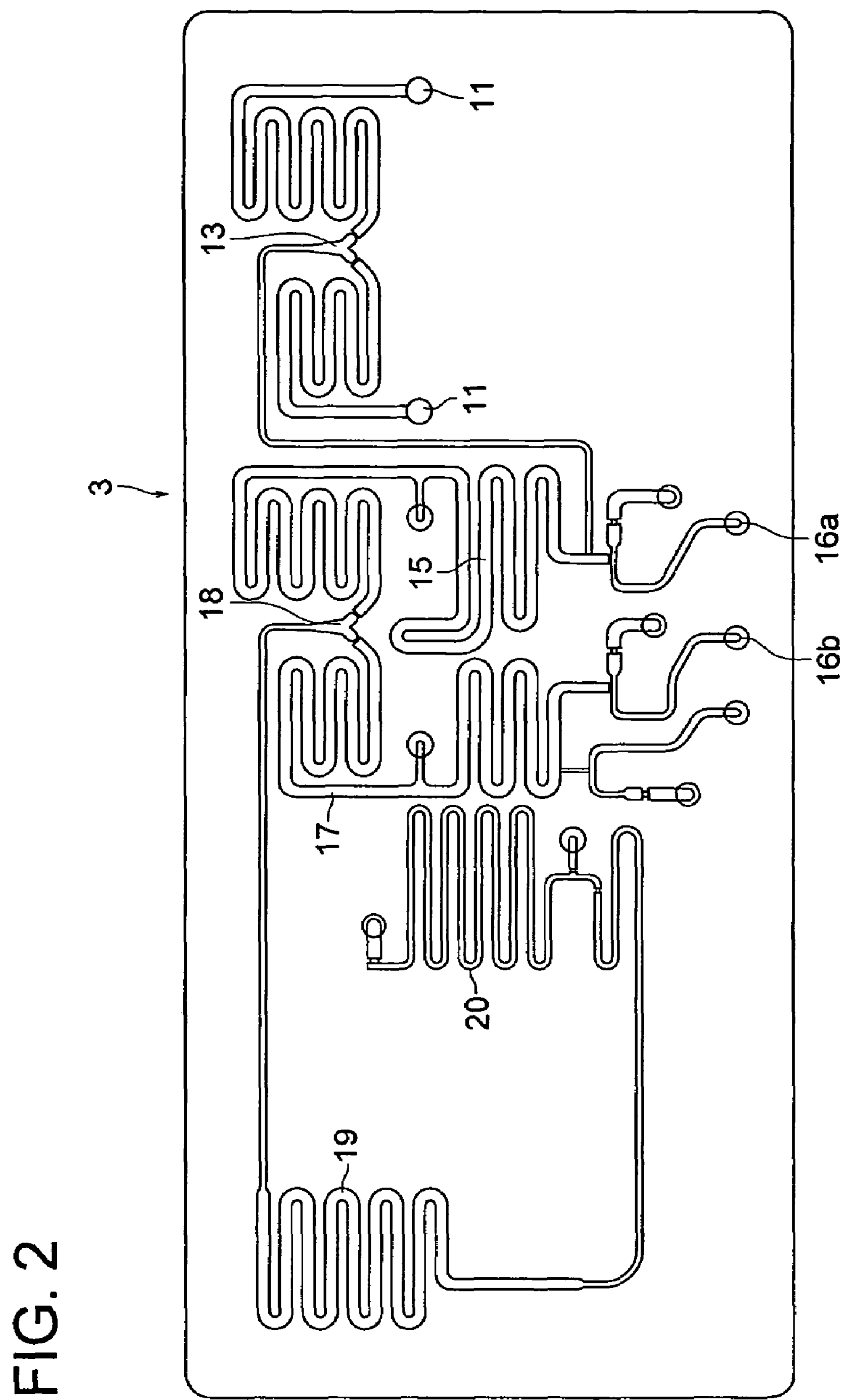
FIG. 2 is a second testing chip in the embodiment.

In the second chip 3, shown in FIG. 2, a series of flow paths are provided so as to mix reagents stored in the first chip 2, cause reaction between the mixed reagent and a specimen, and detect the reaction.

In the testing chip, in accordance with the invention, including the first and second chips, shown in FIGS. 1 and 2, respective flow path elements and structures are disposed at functionally proper positions by a micro processing technology so as to be used as a micro reactor for chemical analyses, various tests, processing and separation of specimen, and chemical synthesis. In the first chip, a plurality of reagent storage sections is provided to store reagents to be used for a predetermined reaction. In some cases, other cleaning liquids, denaturing liquids, or the like may be stored. As described above, reagent is stored in the chip in advance so that a test can be quickly performed regardless of time and place.

The first and second chips can be produced, for example, employing a grooved substrate that is formed with grooves for flow paths or the like in advance on the surface thereof and a covering substrate to be brought into tight contact with the grooved substrate. The grooved substrate is formed with structural parts and flow paths that make these structural parts communicated. Examples of such structural parts are: sections for control of liquid transportation which are liquid reservoir sections including storage sections (such as a reagent storage section and a specimen storage section) and a waste fluid reservoir section, valve sections, liquid feed control sections (such as a water repellant valve shown in FIG. 13 described later), backflow protection sections (such as check valves and active valves), a reagent quantity section, and a mixing section; a reaction section; and a detection section.

The covering substrate may also be formed with such structural parts and flow paths. The covering substrate is brought into tight contact with the grooved substrate to cover these structural parts and flow paths, thereby constructing the first and second chips. Herein, in a case of detecting a reaction in the second chip optically, the detection section, at least, of the structural parts is required to be covered by an optically transparent covering substrate in tight contact between them. Sometimes, more than two substrates are laminated to form a first or second chip.

The first and second chips are usually produced by properly combining more than one forming material. Forming materials can be, for example, plastic resins, various inorganic glasses, silicones, ceramics and metals.

Particularly, chips for test of a large number of measuring specimens subjected especially to risks of contamination and infection are desired to be disposable. Further, since flexibility for multipurpose use and mass-productivity are desired, plastic resins are preferably used as materials for forming chips.

For a substrate such as a grooved substrate where a flow path is formed, plastic materials having water repellency and hydrophobicity with which the flow path hardly distorts due to water absorption and a tiny amount of specimen liquid can be fed without a loss are preferred. These materials are, for example, resin, such as polystyrene, polyethylene, polypropylene, a polyethylene terephthalate, polyethylenenaphthalate, polyethylene vinyl alcohol, polycarbonate, poly methyl pentene, fluorocarbon, and saturation annular polyolefin. Polystyrene is particularly preferred as a material for forming grooved substrates, because polystyrene is excellent in transparency, mechanical characters and formability, which allows easy micro-processing.

In a case where heating up to nearly 100° C. is necessary for analysis, resins that are excellent in heat resistance are used as materials for substrates, of which examples are plastics such as polycarbonate, polyimide, polyether imide, poly benz imidazole, polyetheretherketone.

In order to promote reaction for detection of analyte, a predetermined part or reaction section is often heated up to a desired temperature. An area to be heated is locally heated usually up to about 100° C. On the other hand, there are also cases where it is necessary to cool a specimen, reagent, or the like which becomes unstable at a high temperature. Taking into account such a local rise or fall in local temperature in a chip, it is desired to select a material with a proper heat conductivity. Examples of such materials are resin materials and glass materials. By forming these areas with a material having a small thermal conductivity, heat conduction in the surface direction is inhibited and only an area to be heated can be selectively heated.

In order to optically detect fluorescent material or products of coloring reaction, it is necessary to provide a light transmitting member on the surface of the second chip at least at a part that covers the detection portion of a micro flow path. Therefore, as a material for a covering substrate to cover the detection portion, a transparent material, such as alkali glass, quartz glass and transparent plastic, can be used. Such a light transmitting covering substrate may cover the entire top surface of a testing chip.

Figure 12:
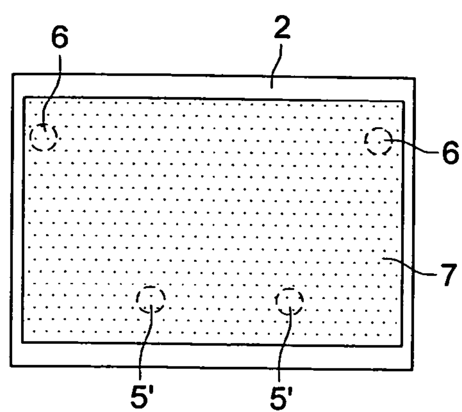
FIG. 12 is a plan view showing a state where upstream-side openings and downstream-side openings of the first chip in FIG. 9 are sealed with a sealing member.

A flow path of a testing chip as a micro reactor is formed according to a path disposition designed on a substrate in advance depending on a purpose. A path in which liquid flows is a micro flow path which is, for example, several dozen to several hundred μm and preferably 50 to 200 μm in width, and 25 to 300 μm and preferably 50 to 100 μm in depth. If the width of the flow path is decreased, the flow path resistance is increased, which may cause a problem in feeding liquid or the like. If the width of the glow path is widened too much, the advantage of a micro scale space is reduced. The longitudinal and lateral sizes of an entire testing chip is typically several dozen millimeters and the height is several millimeters. Herein, in some cases, openings opened outward from one side of the chip, for example, openings 5 and 6 of the first chip in FIG. 1 and openings 11 of the second chip in FIG. 12, are arranged to have a diameter (or longitudinal and lateral lengths) not smaller than 1 mm.

The respective structural parts and flow paths can be formed based on a micro-processing technology in a prior art. Typically, transfer of a microstructure using photosensitive resin through a photolithography technology is preferred. Using the transfer structure, elimination of unnecessary part, adding of necessary parts and transferring of shapes are carried out. After making a pattern, which forms the constructive elements of the chip by a photolithography technology, the pattern is transformed onto a resin. Therefore, as the material of basic substrate on which the micro flow paths of the micro reactor are formed, a plastic resin that can transfer sub-micron structures accurately and is excellent in mechanical characteristics is preferably used. Polystyrene and polydimethylsiloxane are particularly excellent in shape transferring. If necessary, injection molding and extrusion molding can be applied in order to form the respective structural parts and flow paths of the substrate.

A pump connecting section for connection with other micro pumps is provided on the upstream side of the micro flow paths of each of the first and second chips, for example, on the upstream side of storage sections that store reagent, specimen, or the like. Each pump connecting section is provided with flow path openings (for example, the openings 5 in FIG. 1 and Openings 16*a* and 16*b* in FIG. 2) that communicate with the above described storage sections, and driving liquid is fed from these openings by micro pumps to push out the liquid in the respective storage sections toward downstream side.

Figure 3:
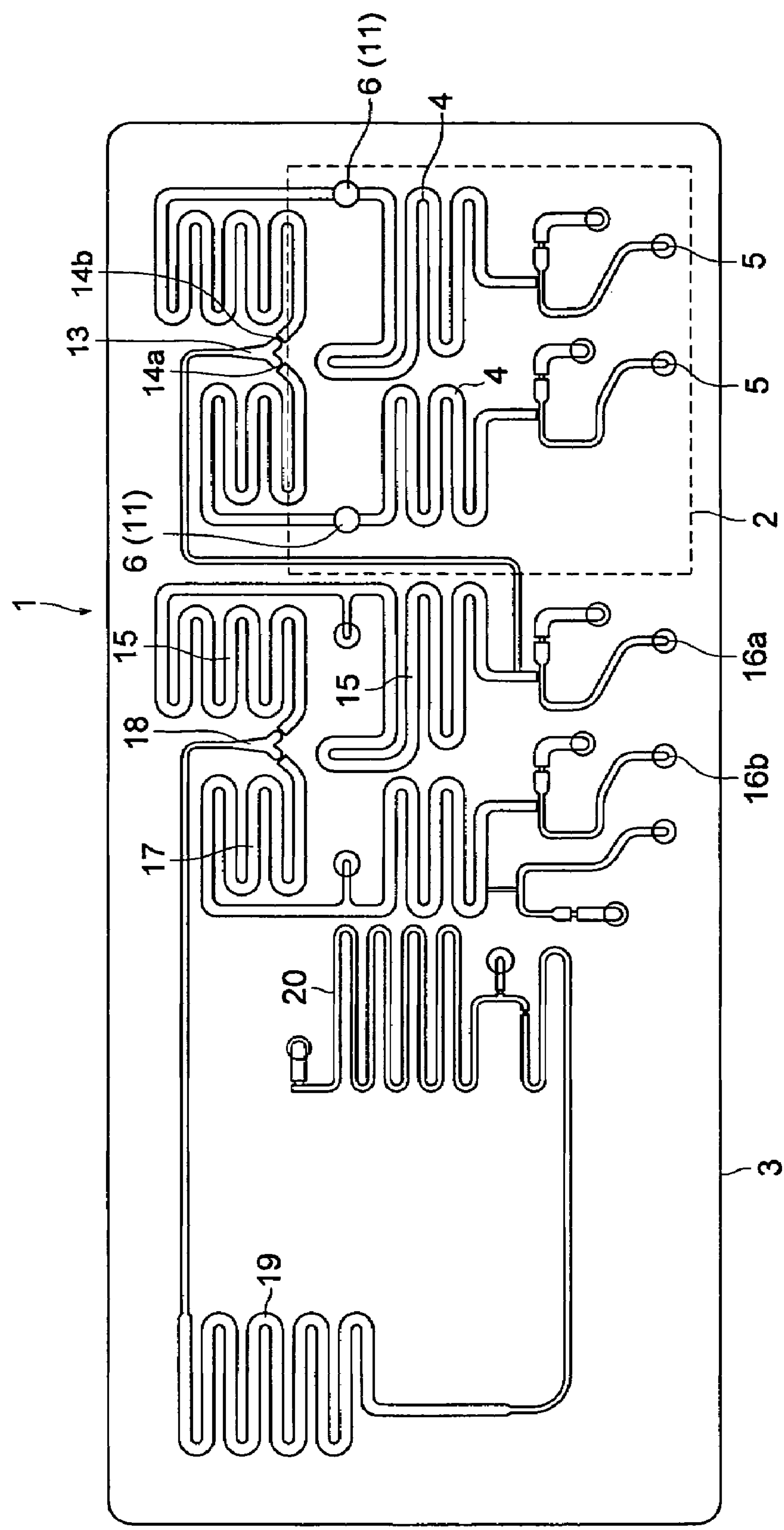
FIG. 3 is a plan view showing the state where the first and second chips in FIGS. 1 and 2 are superimposed on each other.
Figure 4:
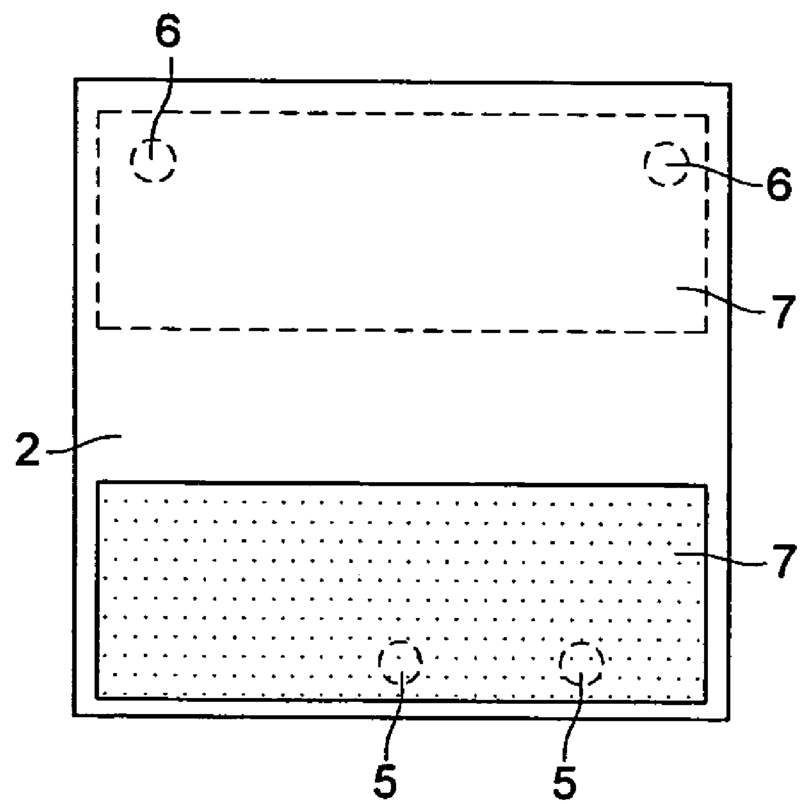
FIG. 4 is a plan view showing the state where an upstream-side opening and a downstream-side opening of the first chip in FIG. 1 are sealed with sealing members.

FIG. 3 shows the state where the first chip in FIG. 1 and the second chip in FIG. 2 are superimposed on each other and the micro flow paths provided therein communicate with each other. In FIG. 3, the openings 6 that are open outward from one side of the first chip 2 and the openings 11 that are open outward from one side of the second chip 3 are positioned on each other correspondingly. The respective reagents sealed in the flow paths 4 of the first chip 2 flow through the respective openings 6 and 11 and reach points just before a confluence section 13.

Figure 13:
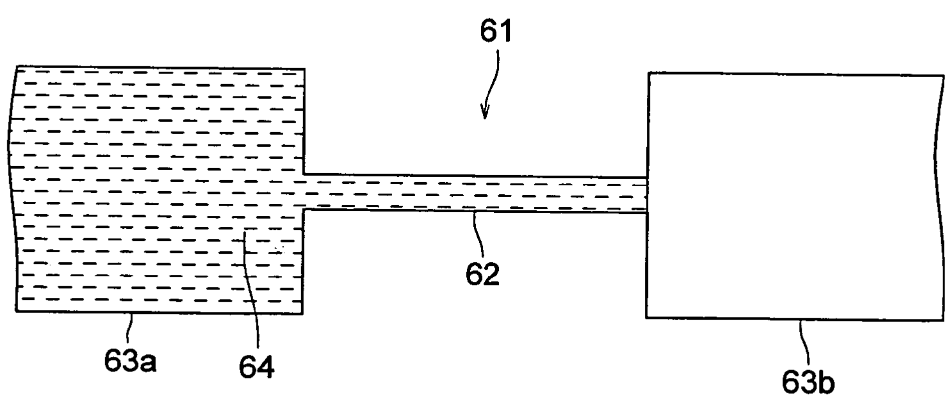
FIG. 13 is a cross-sectional view of a liquid feed control section (water-repellent valve)

Positions 14*a* and 14*b* just before the confluence section 13 are provided with a liquid feed control section 61 (water repellent valve) shown in FIG. 13. Liquid feed control sections 61 are provided, as necessary, also at other positions on micro flow paths, for example, at a confluence section 18 between a mixed reagent and a specimen, in order to control the timing of temporary stop and restart of liquid feeding at these positions.

In FIG. 13, a liquid feed control section 61 is provided with a liquid feed control passage 62. The cross-section area (the cross-sectional area orthogonal to the flow path) of the liquid feed control passage 62 is smaller than those of an upstream-side flow path 63*a* and downstream-side flow path 63*b*.

In FIG. 13, a liquid feed control section 61 is provided with a liquid feed control passage 62. The cross-sectional area (the area of the cross-section orthogonal to the flow path) of the liquid feed control passage 62 is smaller than those of a flow path 63*a* on the upstream side and a flow path 63*b* on the downstream side.

If the walls of the flow paths and passage are made of a hydrophobic material, such as plastic resin, liquid 64 in contact with the liquid feed control passage 62 is inhibited from passing to the downstream-side flow path 63*b* by the difference in surface tension between the liquid 64 and the wall.

In order to flow out the liquid 64 to the downstream-side 63*b*, a liquid feed pressure higher than a predetermined pressure is applied with a micro pump, and the liquid 64 is thus pushed out from the liquid feed control passage 62 to the downstream-side flow path 63*b* against the surface tension. Once the front end portion of the liquid 64 has flowed out from the liquid feed control passage 62 to the downstream-side flow path 63*b*, the liquid flows to the downstream-side flow path 63*b* even without keeping the liquid feed pressure that was required to push out the front end portion of the liquid 64 to the downstream-side flow path 63*b*. That is, the liquid is inhibited from passing through the liquid control passage 62 until the liquid feed pressure reaches a predetermined pressure in the normal direction from the upstream-side to the downstream-side, and if the liquid feed pressure becomes equal to or higher than the predetermined pressure, then the liquid 64 passes through the liquid feed control passage 62.

If the walls of the paths and passage are formed of a hydrophilic material, such as glass, it is necessary to perform coating at least on the inner surface of the liquid feed control passage 62 with a hydrophobic material, such as fluorine material.

In FIG. 3, two kinds of reagents are fed respectively to the positions 14*a* and 14*b* provided with the above described liquid feed control sections, and the liquid feed pressures by the micro pumps are increased to let the reagents pass through the liquid feed control sections so that these reagents meet with each other at the confluence section 13. The mixed reagent is stored into a reagent mixing section 15 and then pushed out to the downstream-side by driving liquid driven by a micro pump that communicates with an opening 16*a* that is open outward from one side of the second chip 3. On the other hand, the specimen stored in the specimen storage section 17 is pushed out to the downstream-side by driving liquid driven by a micro pump that communicates with an opening 16*b* that is open outward from one side of the second chip 3. The mixed regent and specimen meet with each other at a confluence section 18 and get transported to a reaction section 19. For example, the reaction section 19 is heated to start reaction.

The liquid after the reaction is fed to a detection section 20 and a target material is detected, for example, by an optical detection method. FIGS. 1 to 3 show the basic structure of flow path in abstract. Herein, the second chip is provided with a number of openings that communicate with respective different micro pumps so as to push out various reagents (such as a liquid to stop the reaction between the mixed reagent and the specimen, a liquid to perform necessary processing, such as labeling, on the material being the object of detection, a cleaning liquid, etc.) that are stored in advance in flow paths ahead from these openings to the downstream at a predetermined timing, thereby enabling analysis.

Figure 14:
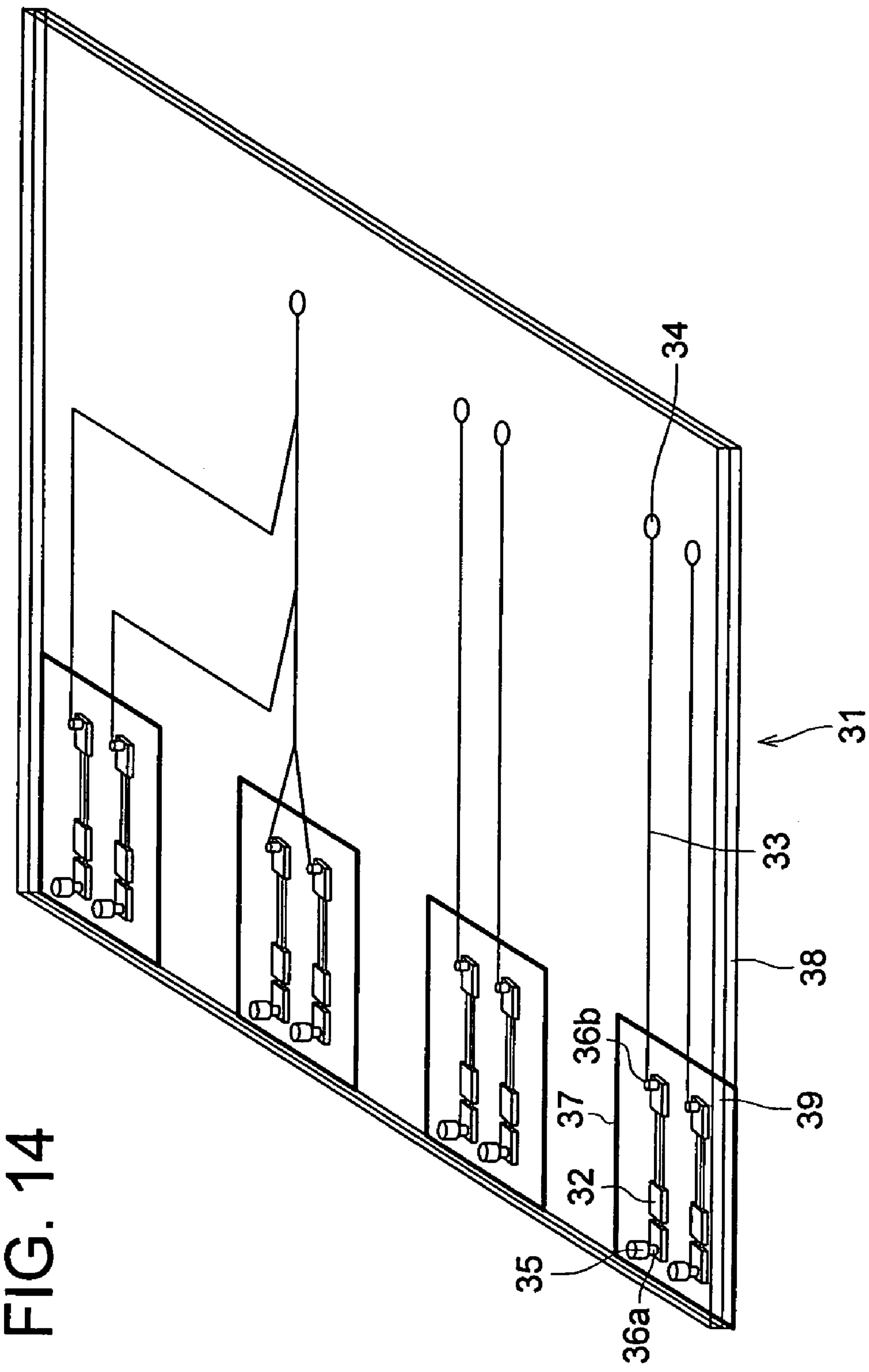
FIG. 14 is a perspective view showing a micro-pump unit in an embodiment of a micro integrates analysis system in accordance with the invention.
Figure 15:
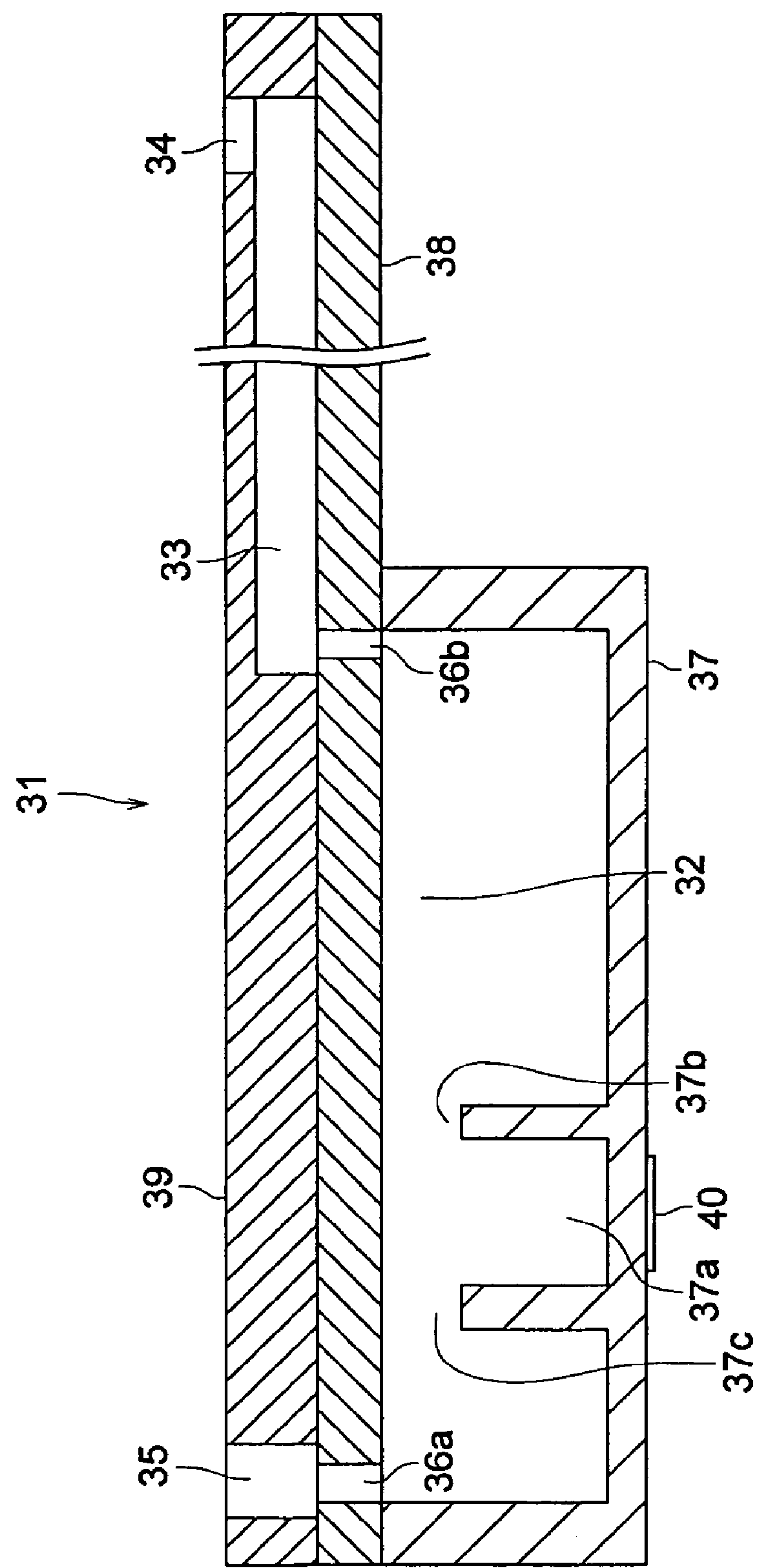
FIG. 15 is a cross-sectional view of the micro-pump unit in FIG. 14.

A number of micro pumps for control of liquid feed in the micro flow paths of the testing chip 1 are integrated in a micro pump unit having a chip shape. FIGS. 14 and 15 show an example of such a micro pump. FIG. 14 is a perspective view of a micro pump unit, and FIG. 15 is a cross-sectional view thereof. Micro pump unit 31 includes three substrates that are a silicon substrate 37, a glass substrate 38 on it, and another glass substrate 39 on the substrate 38. The substrates 37 and 38 are jointed by anodic bonding, and the substrates 38 and 39 are jointed by sealing glass, heat fusing, or hydrofluoric acid bonding.

A micro pump 32 (piezo pump) is arranged by an inner space between a silicon substrate 37 and glass substrate 38 that is stuck on the substrate 37 by anodic bonding. The structure and operation mechanism of the piezo pump are disclosed in the above Patent Documents 2 to 4. Basically, the structure includes a first flow path 37*c* of which flow path resistance varies with a pressure difference, a second flow path 37*c* having a smaller variation rate of the flow path resistance for the variation in pressure difference than that of the first flow path 37*b*, a pressure chamber 37*a* provided between the first flow path 37*b* and the second flow path 37*c*, and an actuator 40 that changes the inner pressure of the pressure chamber 37*a*, driven by voltage. For example, the variation rate of the flow path resistance for the variation in pressure difference in the second flow path 37*c* can be made smaller than that in the first flow path 37*b*, for example, by making the width and height of the first flow path 37*b* equal to those of the second flow path 37*c* and making the length of the first flow path 37*b* shorter than that of the second flow path 37*c*.

The substrate 37 is produced by processing a silicon wafer into a predetermined shape with a photolithography technology. For the substrate 37, there are formed the pressure chamber 37*a*, the first flow path 37*b*, the second flow path 37*c* and the like of the above described piezo pump. At the position of the pressure chamber 37*a*, a diaphragm is formed by processing the substrate 37, and a piezoelectric element being an actuator 40 is adhered on the outer surface of the substrate 37.

A voltage with a predetermined waveform is applied to the actuator 40 to cause vibration of the diaphragm so that the volume of the pressure chamber 37*a* is varied. The voltage on the actuator 40 is controlled such that the displacement rate of the diaphragm toward the direction where the volume of the pressure chamber 37*a* increases and the displacement rate of the diaphragm toward the direction where the volume of the pressure chamber 37*a* decreases are different, thus operating the pump to transport driving liquid.

A flow path 33 is patterned on the substrate 39. On the downstream side of the flow path 33, an opening 34 is provided that is open toward outside from one side of the substrate 39 and communicates with a micro flow path of the testing chip (the first chip). The opening 34 may have a size larger than the width of the flow path 33, if it is necessary to properly position the opening 34 on the opening of the testing chip.

The upstream side of the flow path 33 communicate with the micro pump 32 through a penetrating hole 36*b* of the substrate 38 and a flow path provided in the substrate 37. The upstream side of the micro pump 32 is open toward outside from an opening 35 through an opening 36*a* of the substrate 38. Driving liquid stored in a driving liquid tank is fed out from the opening 35.

Herein, the above micro pump unit 31 is just an example, and it is possible to produce various types of micro pump units formed with micro pumps, flow paths, connecting openings to communicate with a testing chip and a liquid driving tank by a photolithography technology or the like. For example, it is possible to construct a micro pump unit by laminating a glass substrate on a silicon substrate, a photosensitive glass substrate or the like formed with a structure of micro pumps by etching, sticking a PDMS on it, and further on the PDMS, sticking a substrate that is made of plastic, glass, silicon, ceramics or the like and formed with flow path grooves and connecting openings described above.

Further, micro pumps provided on the micro pump unit may not be piezo pumps but may be, for example, check valve type micro pumps.

Operations for using a testing chip in accordance with the invention will be described below.

Figure 5:
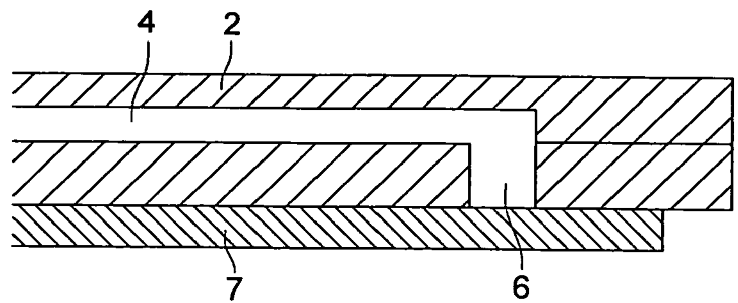
FIGS. 5(*a*) to 5(*c*) are cross-sectional views showing a procedure to superimpose the first and second chips on each other and make micro flow paths of these communicate with each other.
Figure 5:
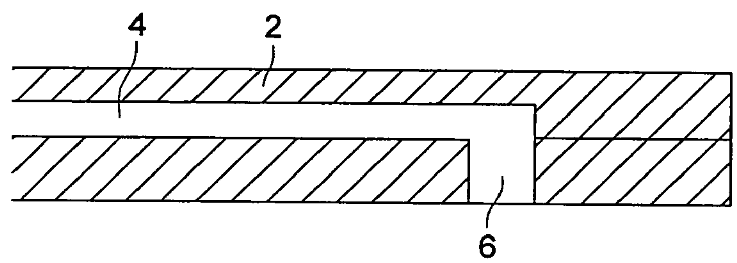
Figure 5:
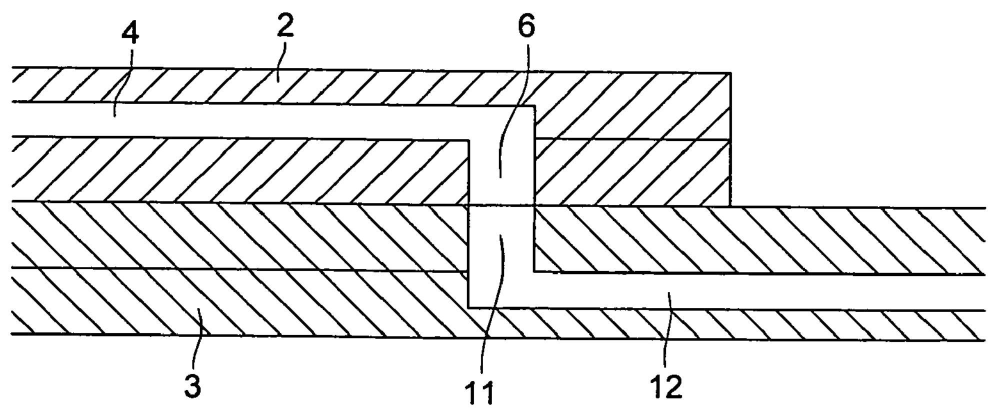

FIGS. 5(*a*) to 5(*c*) are cross-sectional views showing the procedure to superimpose the first and second chips on each other and make micro flow paths thereof communicate with each other. As shown in FIG. 5(*a*), an opening 6 communicating with a flow path 4 of the first chip 2 is sealed with a peelable sealing member 7.

The sealing member 7 is peeled off when the chip is used, as shown in FIG. 5(*b*) so that the opening 6 is exposed. Next, as shown in FIG. 5(*c*), the first chip 2 and the second chip 3 are superimposed on each other with a predetermined position relationship. Thus, the opening 6 of the first chip 2 and the opening 11 of the second chip 3 communicate with each other so that reagent sealed in the first chip 2 can flow into a flow path 12 of the second chip 3.

In order to superimpose the first chip 2 and second chip 3 on each other with a predetermined position relationship and fix them, methods can be applied, such as a method of providing a positioning guide on a chip surface and a method of engaging a recessed portion and protruding portion with each other. Herein, it is necessary to secure enough sealing around the openings 6 and 11 to prevent liquid leakage. To attain this, for example, a sufficient pressure is applied from both sides of a testing chip, at the time of analysis; the peripheries of the openings 6 or 11 are formed of a flexible material such as polytetrafluoroethylene or silicon resin; or a member formed with such materials are disposed around the openings 6 or 11.

Figure 6:
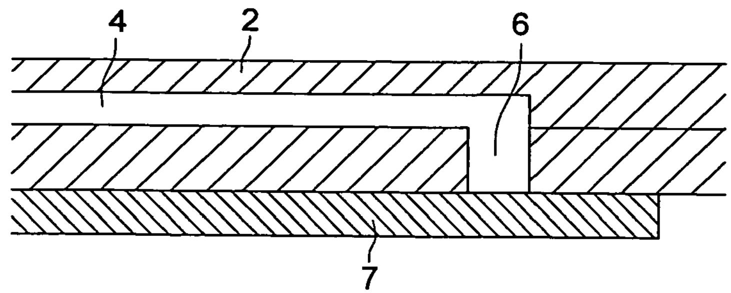
FIGS. 6(*a*) to (*c*) are a cross-sectional views showing a procedure to superimpose a first and second chip on each other and make micro flow paths of these communicate with each other, in another embodiment in accordance with the invention.
Figure 6:
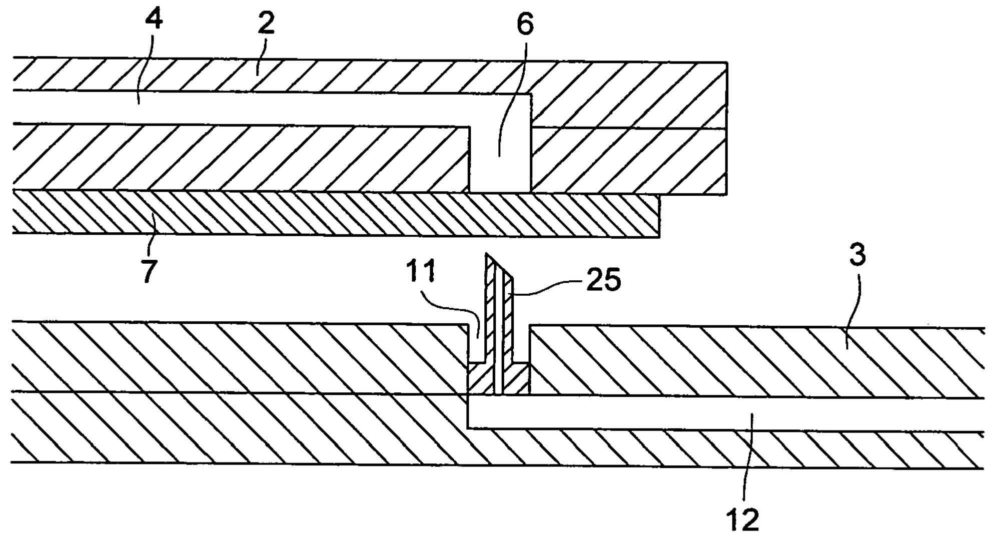
Figure 6:
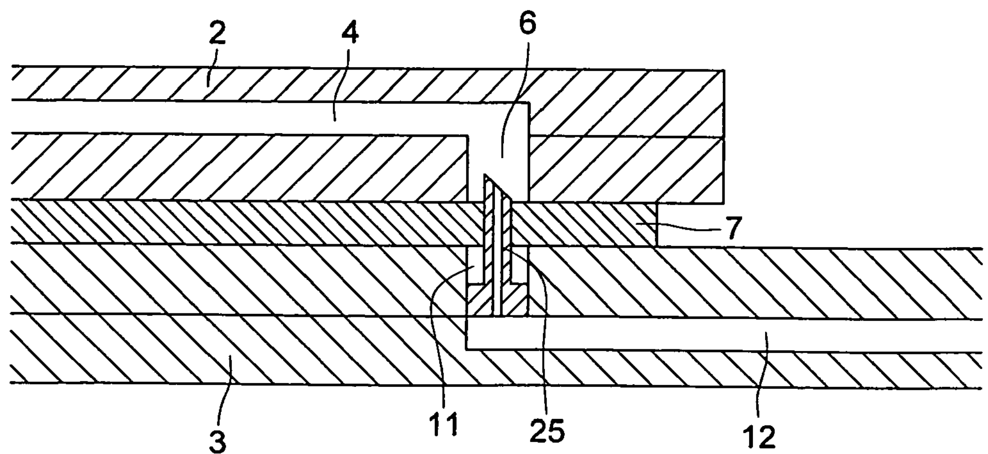

FIGS. 6(*a*) to 6(*c*) are cross-sectional views showing a procedure to superimpose a first and second chip on each other and make micro flow paths of these communicate with each other in another embodiment in accordance with the present invention. As shown in FIG. 6(*a*), an opening 6 communicating with a flow path 4 in the first chip 2 is sealed with a sealing member 7.

On the other hand, as shown in FIG. 6(*b*), needle sections 25 in a thin tube shape are provided at openings 11 of the second chip 3. The first chip 2 and second chip 3 are arranged to face each other with a predetermined position relationship and superimposed on each other as shown in FIG. 6(*c*). Thus, the sealing member 7 of the second chip 3 is pierced by the needle sections 25 at the positions of the openings 6 of the first chip 2, and accordingly, the openings 6 of the first chip 2 and the openings 11 of the second chip 3 communicate with each other. In such a manner, reagent sealed in the first chip 2 can flow into a flow path 12 of the second chip 3 due to capillary function.

For the sealing member 7 stuck to the first chip 2, a material such as a rubber or resin material is preferably employed so as to be easily pierced by the needle sections 25 made of metal or the like.

Figure 7A:
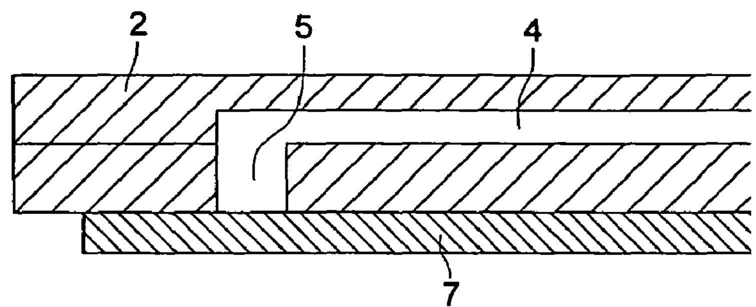
FIGS. 7(*a*) to 7(*c*) are cross-sectional views showing a procedure to superimpose a first chip and a micro pump unit on each other and make a micro flow path of the first chip and a micro pump communicate with each other in still another embodiment in accordance with the invention.
Figure 7B:
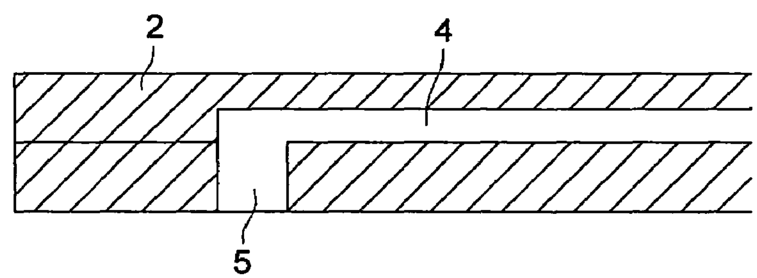
Figure 7C:
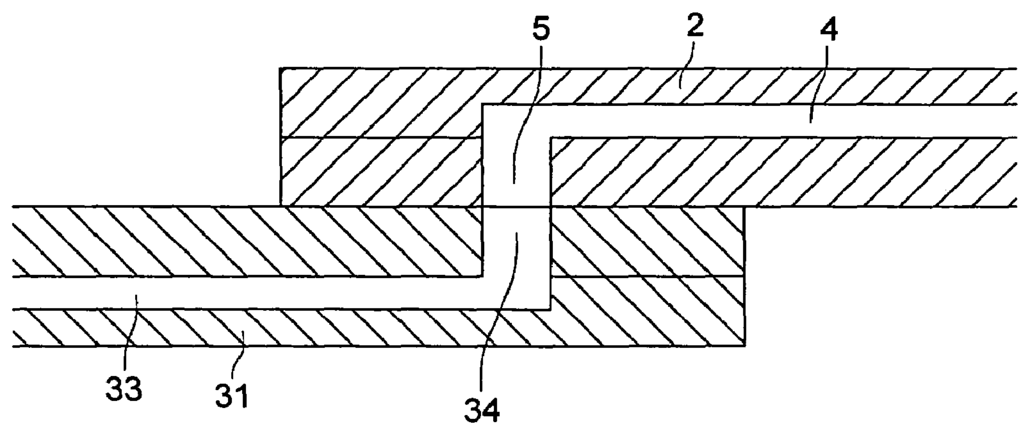

The testing chip structured by integrating the first and second chips in such a manner is connected to a micro pump unit as described above. FIGS. 7(*a*) to 7(*c*) are cross-sectional views showing a procedure to superimpose a first chip 2 and a micro pump unit on each other and make a micro flow path of the first chip 2 and the micro pump communicate with each other.

As shown in FIG. 7(*a*), an opening 5 of the first chip 2 that is on the upstream side of a flow path 4 and communicating with it is sealed by a peelable sealing member 7. When the first chip 2 is used, the sealing member 7 is peeled off and the opening 5 is exposed, as shown in FIG. 7(*b*).

Next, as shown in FIG. 7(*c*), the first chip 2 and the micro pump unit 31 are superimposed on each other with a predetermined position relationship. Thus, the openings 5 of the first chip 2 and the openings 34 of the micro pump unit 31 communicate with each other and driving liquid from the micro pumps flows into the flow paths 4 of the first chip 2.

In order to superimpose the first chip 2 and the micro pump unit 31 on each other with the predetermined position relationship, methods can be employed, such as a method of moving a testing chip in a predetermined direction with a guide member or a method of using a positioning member.

It is necessary to secure enough sealing to prevent liquid leakage around the openings 5 and 34. To attain this, for example, a sufficient pressure is applied from both sides of the testing chip to the portion where the testing chip and the micro pump unit are superimposed on each other, at the time of analysis; the peripheries of the openings 5 or 34 are formed of a flexible material such as polytetrafluoroethylene or silicon resin; or a member formed with such materials are disposed around the openings 5 or 34.

Figure 8:
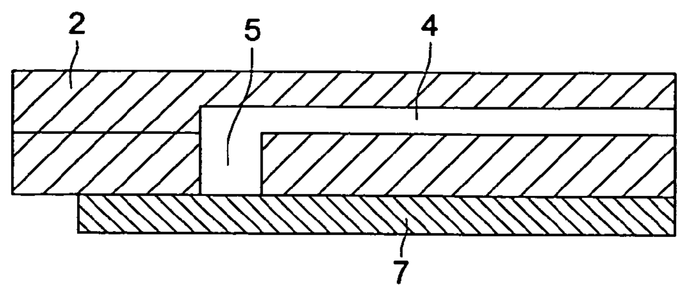
FIGS. 8(*a*) to 8(*c*) are cross-sectional views showing a procedure to superimpose a first chip and a micro pump unit on each other and make micro a flow path of the first chip and a micro pump communicate with each other, in yet another embodiment in accordance with the invention.
Figure 8:
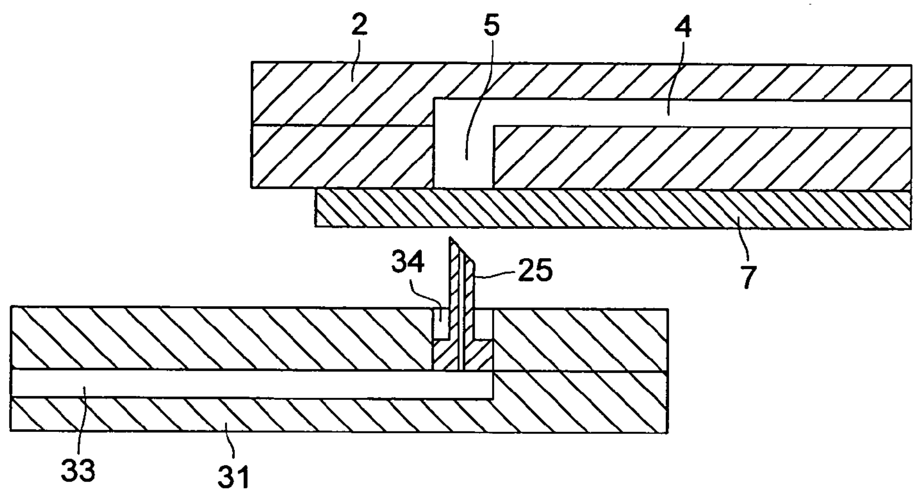
Figure 8:
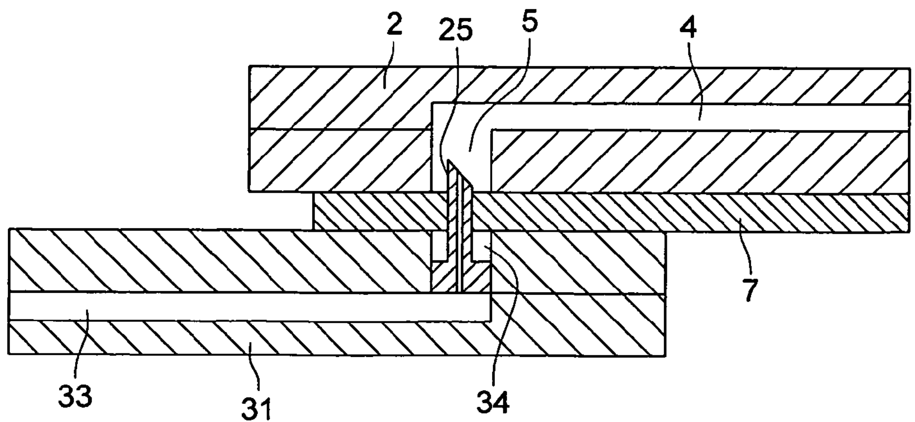

FIGS. 8(*a*) to 8(*c*) are cross-sectional views showing a procedure to superimpose a first chip and a micro pump unit on each other and make a micro flow path of the first chip and a pump communicate with each other in still another embodiment in accordance with the present invention. As shown in FIG. 8(*a*), an opening 5 communicating with a flow path 4 in the first chip 2 is sealed with a sealing member 7.

On the other hand, as shown in FIG. 8(*b*), a needle section 25 in a thin tube shape is provided at an opening 34 of the micro pump unit 31. The first chip 2 and the micro pump unit 31 are arranged to face each other with a predetermined position relationship and superimposed on each other as shown in FIG. 8(*c*). Thus, the sealing member 7 of the micro pump unit 31 is pierced by the needle section 25 at the position of the opening 5 of the first chip 2, and accordingly, the opening 5 of the first chip 2 and the opening 34 of the micro pump unit 31 communicate with each other. In such a manner, driving liquid from the micro pump can flow into the flow paths 4 of the first chip 2.

Figure 9:
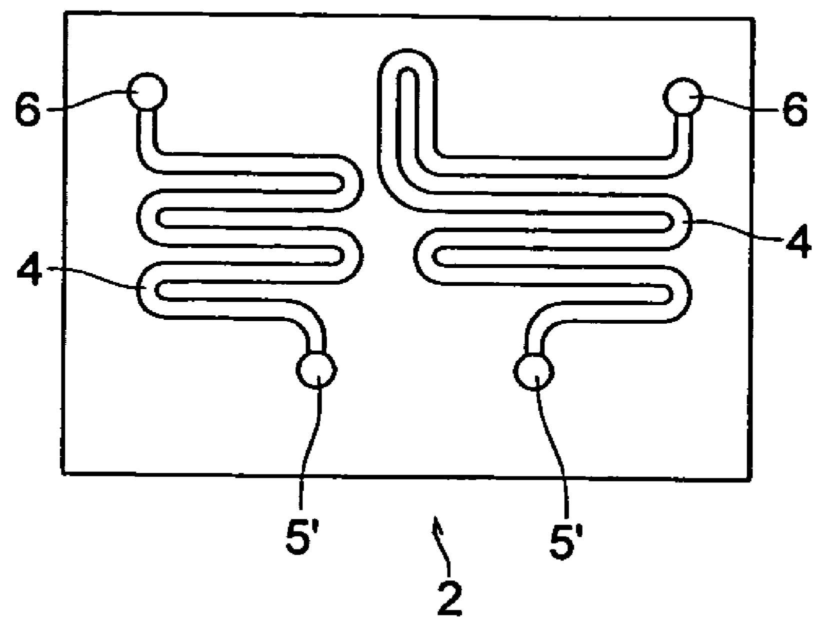
FIG. 9 is a plan view showing a first chip in still another embodiment in accordance with the invention.
Figure 10:
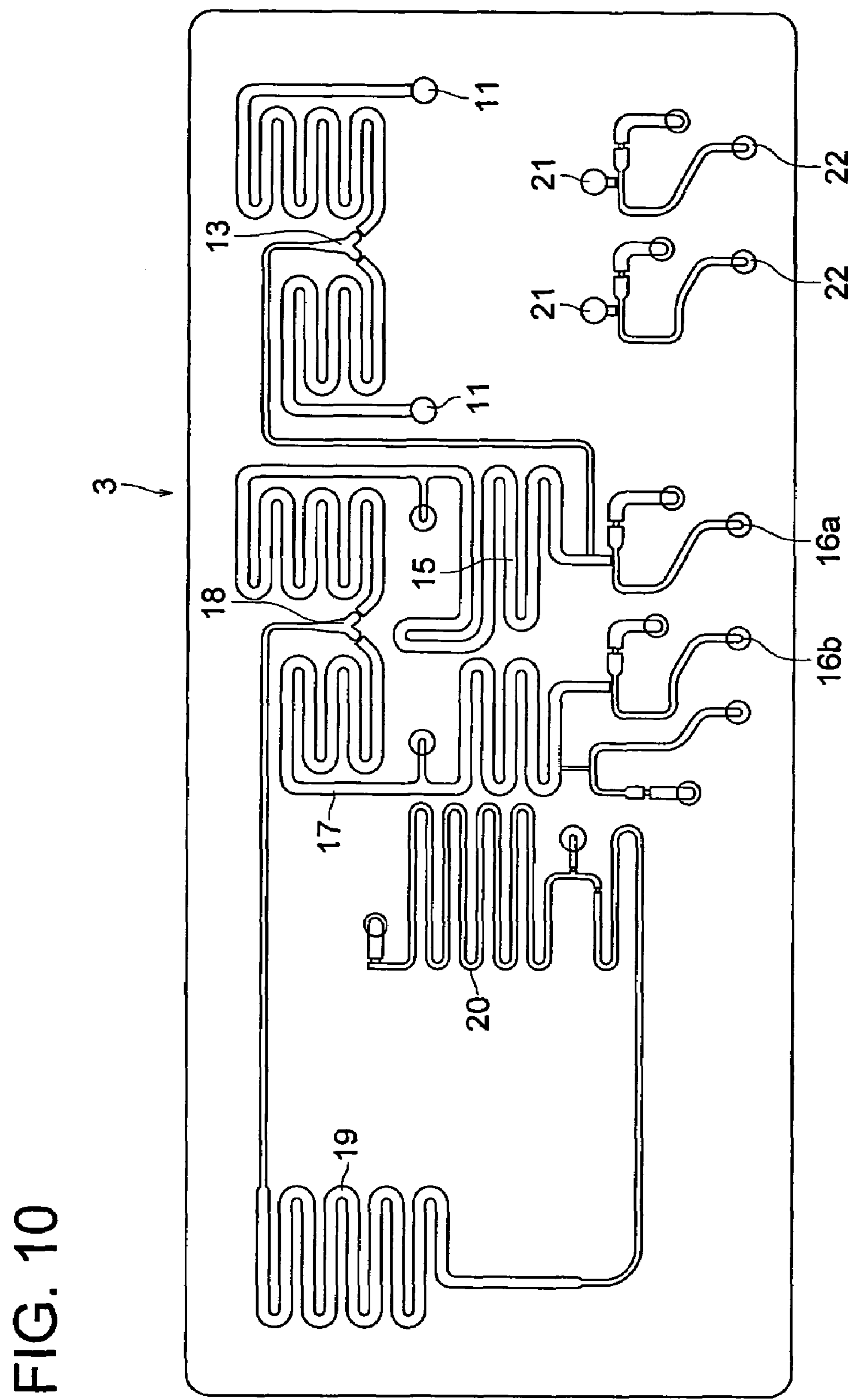
FIG. 10 is a plan view showing a second chip in another embodiment in accordance with the invention.

FIG. 9 is a plan view showing a first chip in yet another embodiment in accordance with the invention and FIG. 10 is a plan view showing a second chip.

As shown in FIG. 9, openings 5' and 6 provided at the both end portions of flow paths 4, of the first chip 2 in the present embodiment, storing reagent are disposed on the same plane. On the other hand, as shown in FIG. 10, the second chip 3 is provided with openings 21 that are to be positioned on the openings 5' of the first chip 2 and provided with pump-side openings 22 communicating with the openings 21.

A sealing member 7 is stuck to the face provided with the openings 5' and 6 of the first chip 2, as shown in FIG. 12, during storage, and the openings 5' and 6 are sealed with the sealing member 7.

Figure 11:
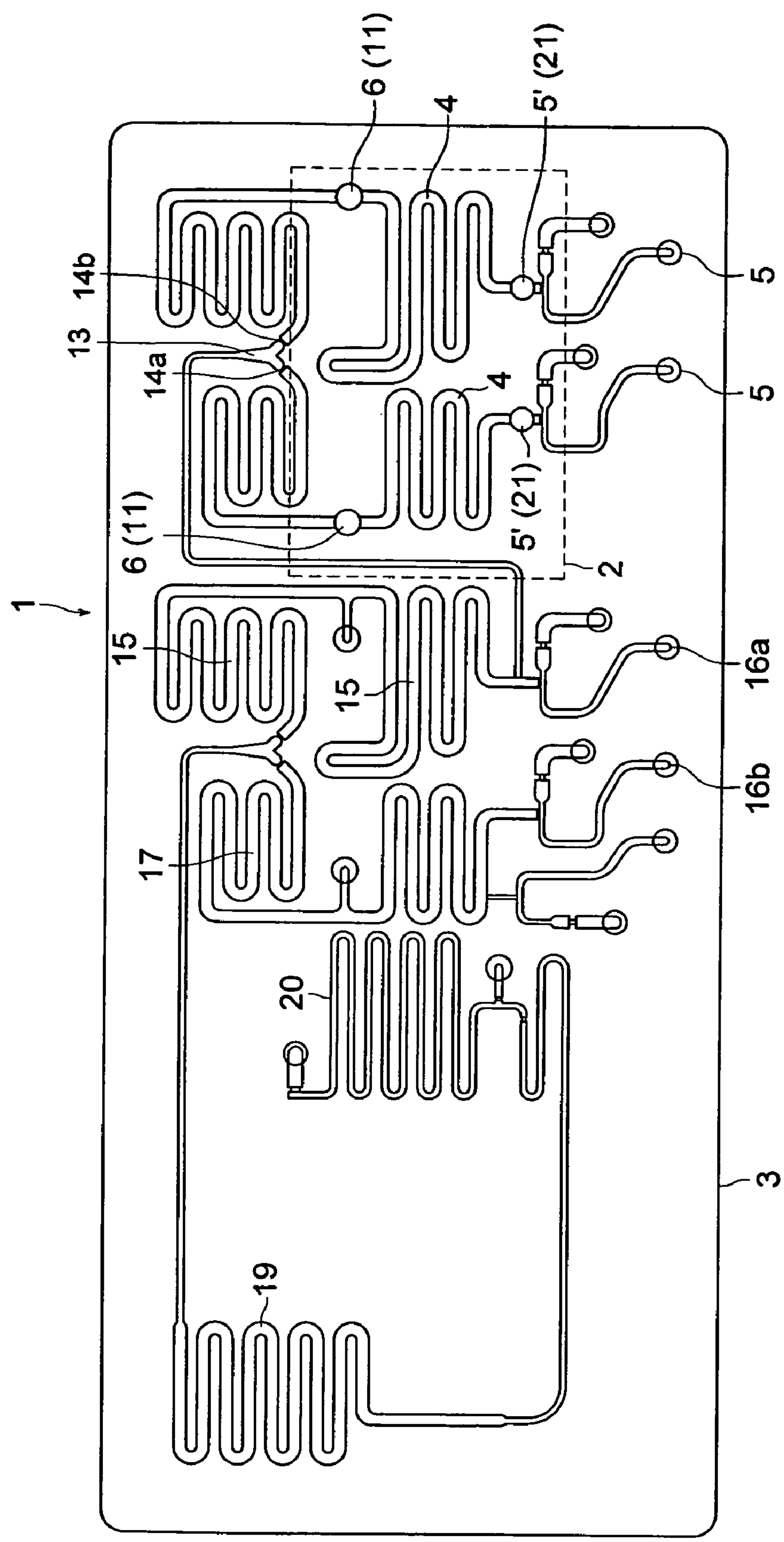
FIG. 11 is a plan view showing a state where the first chip in FIG. 9 and the second chip in FIG. 2 are superimposed on each other.

When the testing chip is used, the openings 6 of the first chip 2 and the openings 11 of the second chip 3 are positioned on each other, the openings 5' of the first chip 2 and the openings 21 of the second chip 3 are positioned on each other, and in such a state, the first chip 2 is superimposed on the second chip 3, as shown in FIG. 11.

The method of making the openings communicate with each other when these chips are superimposed on each other is the same as shown in FIGS. 5(*a*) to (*c*) or FIGS. 6(*a*) to 6(*c*). That is, by superimposing the chips on each other after peeling off the sealing member, as shown in FIGS. 5(*a*) to 5(*c*), the openings are positioned on each other and communicated with each other, or needle sections in a thin tube shape, as shown in FIGS. 6(*a*) to 6(*c*), are provided at the openings 11 and 21 of the second chip and thus the chips are superimposed on each other so that the needle sections pierce the sealing member and thus the openings communicate with each other.

An opening 22, on the pump side, of the second chip 3 is positioned on an opening 34 of the micro pump unit 31, shown in FIGS. 14 and 15. In such a manner, micro pumps 32 and flow paths 4 of the first chip 2 communicate with each other through the flow paths between the openings 21 and the pump side openings 22 of the second chip 3.

<Micro Integrated Analysis System>

Figure 16:
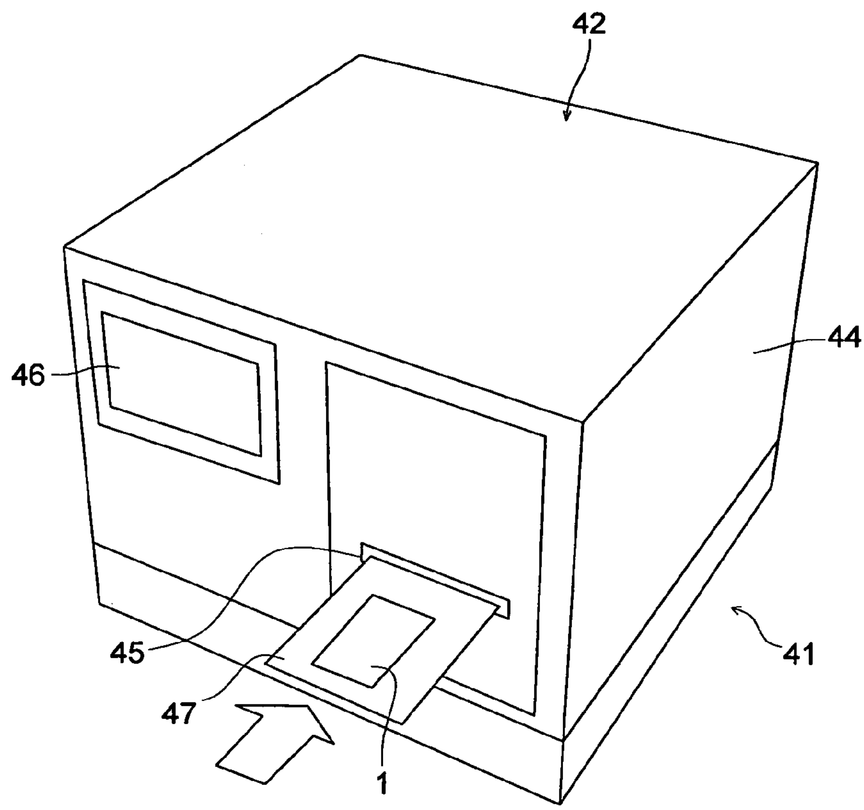
FIG. 16 is a perspective view showing an example of a micro-integrated analysis system.
Figure 17:
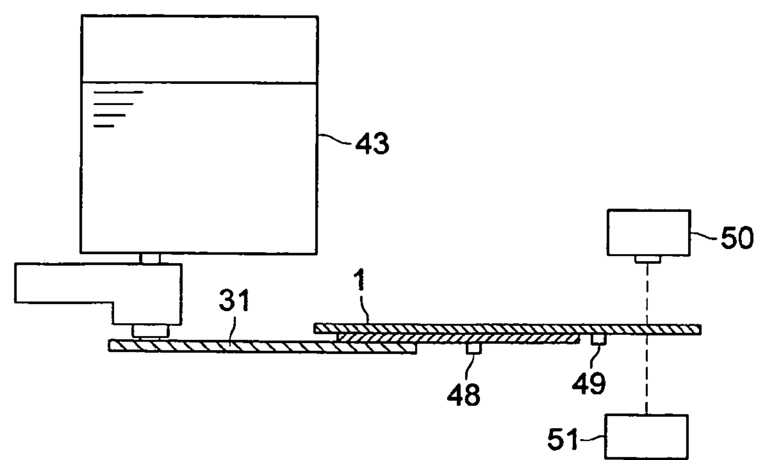
FIG. 17 is a diagram showing the inside structure of the system main body of the micro-integrated analysis system in FIG. 16.

A testing chip is subjected to reaction and analysis in a state, for example, where the testing chip is loaded on a separate main body of a system. The system main body and the testing chip construct an integrated micro analysis system. An example of such an integrated micro analysis system will be described below. FIG. 16 is a perspective view showing an example of an integrated micro analysis system and FIG. 17 is a diagram showing the inner structure of the system main body of this micro integrated analysis system.

The system main body 42 of this micro integrated analysis system 41 includes a storage body 44 in a housing form to store various devices for analysis. A micro pump unit 31, as described above, is disposed inside the storage body 44.

Further, in the storage body 44, there are provided detection processing devices (a light source 50 such as an LED, photomultiplier tube, CCD camera or the like, and a detector 51 for optical detection by a visible spectroscopy method, a fluorescence measurement method, or the like) and a controller (not shown) to control these detection processing devices and the micro pump unit 31. This controller performs control of liquid feeding by micro pumps and control of the detection processing devices that detect reaction in the testing chip 1 with optical means and the like. This controller also performs temperature control of the testing chip 1 with a heating and cooling unit (later described), control of reaction in the testing chip 1, data collection (measurement) and other processings. The micro pumps are controlled by applying driving voltages to the micro pumps, according to a program for which various conditions including the order of liquid feeding, flow rate, timing are set in advance.

The micro analysis system 41 analyzes a target material in a specimen in the testing chip 1 after the testing chip 1 is mounted inside the storage body 44 in a state where the pump connecting section, which is structured by flow path openings provided on the upstream side (for example, the upstream side of the reagent storage section and the specimen storage section) of the micro flow paths of the testing chip 1 and a chip face around the flow path openings, and the chip connecting section 31 of the micro pump unit 31 have been brought into tight liquid contact with each other. The testing chip 1 is loaded onto a conveying tray 47 and introduced from a chip insertion opening 45 into the storage body 44. Herein, the conveying tray 47 is not necessarily required as long as the testing chip 1 can be fixed inside the storage body 44 in a state where the testing chip 1 is pressed against the micro pump unit 31.

A heating and cooling unit (a peltier element 48 and a heater 49) is provided in the storage body 44 in order to locally heat or cool the testing chip 1 mounted at a predetermined position. For example, a peltier element 48 is made in press contact with the area of reagent storage sections of the first chip and a reagent mixing section of the second chip of the testing chip 1 and these areas are selectively cooled, and thereby the reagents are prevented from denaturation or the like. The heater 49 is made in press contact with the area of the flow path of the reaction section in the second chip to selectively heat the reaction section. In this manner, the reaction section is set to a temperature suitable for reaction.

The micro pump unit 31 is connected to a driving liquid tank 43 that communicates with the upstream side of the micro pumps. The micro pumps feed driving liquid of an oil type, mineral oil for example, or an aqueous type such as buffering liquid, which is stored in the driving liquid tank 43, to the storage sections of respective liquids in the testing chip 1 so as to push out the liquid of the respective storage sections by the driving liquid to the downstream side of the testing chip 1.

The serial analysis process including a pre-processing of the specimen being a measurement sample, reaction, and detection is performed in a state where the testing chip 1 is mounted on the system main body 41 in which the micro pumps, detection processing device and the controller are integrated. Preferably, liquid feeding of the sample and reagents, pre-processing, a predetermined reaction after mixing, and optical measurement are automatically performed as a serial continuous process, wherein measured data is stored into a file along with necessary conditions and recording items. Analysis results are displayed on the display section 46 of the storage body 44, as shown in FIG. 16.

An example of reaction between a specimen and reagent and detection of the reaction, using a testing chip, will be described below.

In a preferable example of a testing chip, a first chip includes:

a reagent storage section that stores reagent to be used for probe synthesis reaction and detection reaction (including gene amplification reaction and antigen-antibody reaction);

a positive control storage section that stores positive control;

a negative control storage section that stores negative control; and a probe storage section that stores a probe (for example, a probe that hybridizes a gene, as a detection object, amplified by gene amplification reaction), and a second chip includes:

a specimen storage section into which a specimen or analyte (for example, DNA, RNA, gene) extracted from the specimen is injected;

a specimen pre-processing section that performs pre-processing of the specimen;

a micro path that communicates with the respective storage sections; and a pump connecting section connectable with micro pumps that feed liquid in the respective storage sections and the flow path.

This testing chip is connected with the micro pumps through the pump connecting section, feed a specimen stored in the specimen storage section or biological material (for example, DNA or other biological material) extracted from the specimen and reagent stored in the reagent storage section to the flow path on the downstream side, mixes them at a reaction section of the micro flow path, for example, a section where gene amplification reaction (antigen-antibody reaction, etc. in the case of protein) is performed, and causes reaction between them. Then, the testing chip feeds processed solution as a result of processing the reaction solution and a probe stored in the probe storage section to the detection section that is on the flow path on the downstream side, mixes the processed solution and the probe in the flow path for synthesis (or hybridization), and detects the biological material, based on the reaction product.

Further, positive control stored in the positive control storage section and negative control stored in the negative control storage section are likewise subjected to the above described reaction and detection.

The specimen storage section in the testing chip communicates with a specimen injection section, temporarily stores s specimen and feeds the specimen to a mixing section. The specimen injection section, to which the specimen is injected from the top surface of the specimen storage section, is preferably formed with a plug of an elastic body, of a rubber material for example, to prevent leaking out, infection and contamination and to secure sealing performance, or is covered by a resin or tempered film of polydimethylsiloxane (PDMS) or the like. For example, a specimen in a syringe is injected with a needle which penetrates through a plug of the rubber material or a needle which penetrates through a thin hole with a lid. In the former, it is preferable that the needle hole immediately stops up when the needle is removed. Or, a different type of a specimen injection mechanism may be equipped.

The specimen injected into the specimen storage section is pre-processed, if necessary, prior to mixing with reagent in such a manner, for example, that the specimen is mixed with a processing solution in the specimen pre-processing section that is provided in the flow path. Such a specimen pre-processing section may include a separation filter, adsorption resin, beads or the like. Preferable specimen pre-processing includes separating or condensing of analyte and deproteination. Bacteriolysis and DNA extraction processing are performed by the use of a bacteriolytic agent, for example, 1% SDS mixed solution. DNA is released from inside a cell and gets adsorbed on the surface of beads or a filter in this process.

A predetermined amount of necessary reagent or the like is sealed in the flow path of the first chip in the testing chip. Therefore, it is not necessary to inject a necessary amount of reagent each time of using the chip, and the chip is always ready to be used. In the analysis of a biological material in a specimen, respective reagents necessary for measurement are usually known. For example, for analysis of an antigen present in a specimen, an antibody against it, and preferably, a monochronal antibody is used. The antibody is preferably labeled with FITC.

Reagents to be used for gene testing include various reagents used for gene amplification, probes used for detection, chromophore reagents, and, if necessary, pre-processing reagents to be used for pre-processing of the specimen.

Driving liquid is supplied from micro pumps to push out specimen solution and reagent solution from the respective storage sections and make them meet with each other, and thus necessary reactions starts, such as gene amplification reaction, trapping of analyte, and antigen-antibody reaction.

As a method of DNA amplification, PCR amplification method can be adopted, which is disclosed in various literatures including improvements and widely applied in various fields. A PCR amplification method requires temperature control to raise and drop temperature between three temperatures, and for which a flow path device capable of suitable temperature control for a microchip has been already offered by the inventors (TOKKAI No. 2004-108285). This device system can be applied to the amplification path of a chip in accordance with the invention. With this device system, the heating cycle is switched at a high speed, and the micro flow path is arranged as a micro reaction cell with a small thermal capacity. Therefore, DNA amplification can be performed in much shorter time than a conventional manual method.

ICAN method (Isothermal chimera primer initiated nucleic acid amplification method), which has been recently developed, is a preferable amplification technology also for a system in accordance with the invention, because it enables DNA amplification at an arbitrary constant temperature in the range of 50 to 65° C. in a short time (Patent No. 3433929). This method, which takes an hour by manual work, takes only 10 to 20 minutes and preferably 15 minutes with a system in accordance with the invention, including analysis.

On the downstream side from the reaction section of the micro flow path of the testing chip, there is provided a detection section to detect, for example, an amplified gene. A transparent material, and preferably a transparent plastic is employed, at least, for the detection section to enable optical measurement.

Protein with biotin affinity (avidin and streptavidin) adsorbed on the detection section on the micro flow path is specifically bound to biotin labeled with a probe material or biotin labeled at the 5' end of primer used for gene amplification reaction. Thus, a probe or an amplified gene labeled with biotin is trapped at the detection section.

The method for detection of separated analyte or DNA of an amplified objective gene is not particularly limited, however, basically executed in the following processes, as a preferable embodiment.

(1a)

A specimen or DNA extracted from the specimen, or cDNA synthesized by reverse transcription from a specimen or RNA extracted from the specimen, and a primer that is biotin-modified at the 5' end are fed out to a micro flow path on the downstream side from their storage sections.

After gene amplification reaction is performed at the reaction section in the micro flow path, amplification reaction solution including the gene having been amplified in the micro flow path and denaturation solution are mixed, the amplified genes are made into a single strand by denaturation, and then the single strand and a probe DNA fluorescent-labeled with FITC (fluorescein isothiocyanate) at the end are hybridized.

Next, the hybrid is transported to the detection section, in the micro flow path, which adsorbed the protein with biotin affinity, and thereby the amplified gene is trapped at the detection section in the micro flow path (the amplified gene may be hybridized with the probe DNA after having been trapped at the detection section).

(1b)

The specimen is mixed with a reagent that contains a specific antibody against an antigen, metabolite, or analyte such as hormone present in the specimen, preferably a monochronal antibody. In this case, the antibody is labeled with biotin and FITC. Therefore, the product resulted from the antigen-antibody reaction contains biotin and FITC. This product is transported to the detection section and fixed to the detection section through binding between the protein with biotin affinity and the biotin.

(2)

Gold colloid solution of which surface is modified with an anti FITC antibody which specifically binds with FITC is flowed in the micro flow path, and thus, this gold colloid is adsorbed on FITC of the fixed analyte/antibody reaction product, or on the FTIC modified probe having been hybridized with the gene.

(3)

The concentration of the gold colloid in the micro flow path is optically measured.

An embodiment in accordance with the invention has been described above, however, the invention is not limited thereto and various changes and modifications may be made without departing from the spirit of the invention.

With a testing chip in accordance with the invention, reagent that is sealed at a predetermined position in a flow path in advance is prevented from leaking out to an external flow path during storage, and is it possible to easily flow out the reagent from a flow path in which the reagent is sealed to a successive flow path at the time of use.

What is claimed is:

1. A testing chip, comprising:

(1) a first chip that includes:

a micro flow path that stores reagent;

an upstream-side opening provided on an upstream-side of the micro flow path;

a downstream-side opening provided on a downstream-side of the micro flow path; and one or more sealing members in a small thickness that are stuck to at least one surface of the first chip to respectively seal the upstream-side opening and the downstream-side opening until the testing chip is used; and (2) a second chip that includes:

a micro flow path for mixing and reaction between reagent and a specimen and detecting the reaction; and an opening provided on an upstream side of the micro flow path, wherein, when the testing chip is used, the first and second chips are superimposed on each other such that the downstream-side opening of the first chip and the opening of the second chip are positioned on each other.

2. The testing chip of claim 1, wherein:

the sealing member that seals the downstream-side opening of the first chip is peelable;

the sealing member is peeled off when the testing chip is used; and thereafter, the first and second chips are superimposed on each other so that the micro flow path of the first chip and the micro flow path of the second chip communicate with each other.

3. The testing chip of claim 1, wherein:

a needle section in a thin-tube shape is provided at the opening of the second chip;

the first and second chips are superimposed on each other when the testing chip is used so that the needle section penetrates through the sealing member at a position of the downstream-side opening of the first chip to make the micro flow path of the first chip and the micro flow path of the second chip communicate with each other.

4. The testing chip of claim 1, wherein the upstream-side opening of the first chip is positioned on an opening of a micro pump unit in a chip form, the opening of the micro pump unit communicating with a micro pump and a downstream-side of the micro pump.

5. The testing chip of claim 4, wherein:

the sealing member that seals the upstream-side opening of the first chip is peelable and peeled off when the testing chip is used;

the testing chip of which the first and second chips are superimposed on each other thereafter is superimposed on the micro pump unit such that the upstream-side opening of the first chip and the opening of the micro pump unit are positioned on each other to make the micro flow path of the first chip and the micro pump communicate with each other.

6. The testing chip of claim 4, wherein when the testing chip is used, the testing chip of which the first and second chips are superimposed on each other is superimposed on the micro pump unit that is provided with a needle section in a thin-tube shape at the opening thereof so that the needle section penetrates through the sealing member at a position of the upstream-side opening of the first chip to make the micro flow path of the first chip and the micro pump communicate with each other.

7. The testing chip of claim 1, wherein the micro flow path of the second chip is provided with:

an opening A to be positioned on the upstream-side opening of the first chip by superimposing the first and second chips on each other when the testing chip is used;

and a pump-side opening B to be positioned on an opening of a micro pump unit in a chip form, the opening of the micro pump unit communicating with a micro pump and a downstream side of the micro pump.

8. The testing chip of claim 7, wherein:

the sealing member that seals the upstream-side opening of the first chip is peelable and peeled off when the testing chip is used; and the first and second chips are superimposed on each other thereafter so that the micro flow path of the first chip and the micro flow path of the second chip communicate with each other, the micro flow path of the second chip communicating with the pump-side opening.

9. The testing chip of claim 7, wherein:

a needle section in a thin-tube shape is provided at the opening A of the second chip;

the first and second chips are superimposed on each other when the testing chip is used so that the needle section penetrates through the sealing member at a position of the upstream-side opening of the first chip to make the micro flow path of the first chip and the micro flow path of the second chip communicate with each other, the micro flow path of the second chip communicating with the pump-side opening B.

10. A micro integrated analysis system, comprising:

the testing chip of claim 1 and a system main body, wherein the system main body includes inside a housing thereof:

a micro pump unit in a chip form having a plurality of micro pumps and openings that communicate with the micro pumps and are to be positioned on upstream-side openings of the testing chip;

a driving liquid tank that communicates with an upstream-side of the micro pumps and stores driving liquid that pushes reagent from an upstream-side to feed the reagent to a downstream-side of a micro flow path of the testing chip and;

a detection processing device to detect reaction in the testing chip; and a control device that controls the micro pump unit and the detection processing device;

wherein, the system analyses a target material in a specimen in a state where the testing chip is mounted on the system main body.

* * * * *